United States Patent [19]

Hoelderich et al.

[11] Patent Number: 4,503,281

[45] Date of Patent: Mar. 5, 1985

[54] PREPARATION OF $C_2$-$C_4$-OLEFINS FROM METHANOL/DIMETHYL ETHER

[75] Inventors: Wolfgang Hoelderich; Wolf D. Mross, both of Frankenthal; Matthias Schwarzmann, Limburgerhof, all of Fed. Rep. of Germany

[73] Assignee: BASF Aktiengesellschaft, Fed. Rep. of Germany

[21] Appl. No.: 577,762

[22] Filed: Feb. 7, 1984

[30] Foreign Application Priority Data

Feb. 10, 1983 [DE] Fed. Rep. of Germany ....... 3304479

[51] Int. Cl.$^3$ .............................................. C07C 1/20
[52] U.S. Cl. .................... 585/640; 585/408; 585/469; 585/733; 502/202
[58] Field of Search ............... 585/640, 408, 469, 733, 585/639; 502/202

[56] References Cited

U.S. PATENT DOCUMENTS

| | | | |
|---|---|---|---|
| 4,254,297 | 3/1981 | Frenken et al. | 585/640 |
| 4,292,458 | 9/1981 | Klotz | 585/640 |
| 4,423,273 | 12/1983 | Hoelderich et al. | 585/640 |
| 4,433,188 | 2/1984 | Hoelderich et al. | 585/640 |

FOREIGN PATENT DOCUMENTS 0075203 9/1981 European Pat. Off. ............ 585/640

Primary Examiner—Delbert E. Gantz
Assistant Examiner—A. Pal
Attorney, Agent, or Firm—Keil & Weinkauf

[57] ABSTRACT

$C_2$-$C_4$-olefins are prepared by catalytic conversion of methanol and/or dimethyl ether in the presence of a zeolite catalyst at elevated temperatures, by a process in which the catalyst used is a pure borosilicate zeolite which has been tableted or extruded without a binder and treated with hydrofluoric acid and hydrochloric acid. The treatment of the catalyst with hydrofluoric acid is carried out using 0.001-1N HF, and that with hydrochloric acid is carried out using 3-25% strength acid. The time-on-stream of the catalyst is improved.

4 Claims, No Drawings

PREPARATION OF $C_2$-$C_4$-OLEFINS FROM METHANOL/DIMETHYL ETHER

Recently, efforts to prepare olefins from methanol have become increasingly important. Methanol can be readily produced from coal, via coal gasification and the production of synthesis gas, with the aid of welltried technology. If it were possible to convert methanol to lower olefins in an economical manner, the further processing methods which are conventional in the chemical industry today and employ coal as a raw material, could also be preserved. In the past few years, processes have therefore been developed with the object of preparing olefins from methanol and/or dimethyl ether.

Such a process is described in, for example, German Laid-Open Application DOS No. 2,615,150. In this process, the catalyst used is a ZSM-5 aluminosilicate zeolite, which is in fact an aromatization catalyst. However, by means of various measures, in particular by reducing the residence time, the conversion can be steered in the direction of olefin formation. Other factors which favor olefin formation are, in particular, dilution of the methanol and the dimethyl ether with an inert gas and steam, respectively. Experience has shown that high olefin yields are obtainable only when methanol and/or dimethyl ether are very substantially diluted with an inert gas or steam. Other conventional processes have the disadvantage that the catalyst can be subjected only to a low load and is rapidly coked. Dilution of the catalyst with a binder is also said to be an advantageous measure for olefin formation, but the binders used cause side reactions as well as deactivation of the catalyst.

We have found that $C_2$-$C_4$-olefins are obtained in high yield by catalytic conversion of methanol and/or dimethyl ether at elevated temperatures, in the presence of a zeolite catalyst, if the catalyst used is a pure borosilicate zeolite which has been tableted or extruded in the absence of a binder and treated with hydrogen fluoride and/or hydrochloric acid.

Advantageously, the catalyst used is one which has been treated with hydrofluoric acid, preferably 0.1 N HF, and then with hydrochloric acid, preferably 15% strength HCl, thoroughly washed, dried at 100° C. and calcined at 500° C. An essential feature of the invention is that the two measures (hydrofluoric acid treatment and hydrochloric acid treatment) carried out in succession have a more advantageous effect than the individual measures on the catalytic properties of the catalyst.

In a preferred process for the preparation of the catalyst used according to the invention, the borosilicate zeolite, which is present in the ammonium form after synthesis, is converted to the acidic H form by calcination at 540° C. for 16 hours, and this calcined product is treated with a 0.001–1 N, preferably 0.05–0.2 N, hydrofluoric acid for from 1 to 3 hours and at from 60° to 80° C. The treated zeolite is filtered off, washed thoroughly, dried at from 100° to 140° C. and then calcined at from 500° to 600° C. for 5 hours. This measure can be followed by treatment with 3–25, in particular 10–18, % strength hydrochloric acid at from 60° to 80° C. for from 1 to 3 hours. The resulting product is filtered off, washed thoroughly until Cl ions are no longer detectable in the wash water, dried at from 100° to 140° C. and calcined at from 500° to 600° C. for 5 hours. This treatment of the catalyst with hydrochloric acid can also be carried out alone, without the treatment with hydrofluoric acid.

The acid treatments are essential to the reactivity of the catalyst; the pure untreated borosilicate zeolite reacts only at above 550° C. or when the olefins are fed in or recycled or pure dimethyl ether is used. However, the olefin yields obtained are poorer than those obtained with binder-containing catalysts under the same conditions. The acid treatments enable methanol to be chemisorbed onto the pure borosilicate zeolite and to be dehydrated to dimethyl ether, whose formation is a precondition for the reaction.

In carrying out the process, methanol, which is in equilibrium with dimethyl ether, is converted over the catalysts described above, under a pressure from atmospheric pressure to about 30 bar, preferably from 0 to 1 bar, and at from 300° to 650° C., preferably from 400° to 550° C. The methanol may contain as much as 90% by weight of water, but it is advantageous if the starting material used is crude methanol containing about 20% of water.

Other lower alcohols may also be admixed to the methanol. The space velocity, expressed as WHSV in $h^{-1}$, i.e. g of methanol and/or dimethyl ether per g of catalyst per hour, is advantageously chosen such that highly quantitative conversion of the starting materials takes place, so that separation and recycling problems with regard to unconverted dimethyl ether do not arise. In general, therefore, the WHSV is from 0.5 to 50 $h^{-1}$, preferably from 2 to 15 $h^{-1}$.

The novel process results in a substantial increase in the selectivity with respect to $C_2$-$C_4$-olefins in the conversion of methanol to hydrocarbons, in particular at from 400° to 600° C.

The undesirable by-products methane and aromatics, whose formation is due in part to the binder, are substantially suppressed as a result of using the novel catalyst. This is advantageous, resulting in an increase in the time-on-stream of the catalyst used.

The time-on-stream is the time between regenerations. The total life of the catalyst is also prolonged. The improvement in the time-on-stream in accordance with the invention is particularly advantageous when the conversion is carried out at elevated temperatures, e.g. from 450° to 550° C.

The fact that extrusion or tableting of the borosilicate zeolites with a binder is dispensed with is also of economic importance. Another advantage of the invention is that the conversion to $C_2$-$C_4$-olefins can be carried out using crude methanol without the addition of inert diluents, e.g. $N_2$, He or $H_2O$.

The Examples which follow illustrate the process according to the invention.

EXAMPLES

The boron zeolite is synthesized hydrothermally from 64 g of finely divided $SiO_2$, 12.2 g of $H_3BO_3$ and 800 g of an aqueous 1,6-hexanediamine solution (50:50 mixture) at 170° C. under autogenous pressure in a stirred autoclave. The crystalline product is filtered off, washed, dried for 24 hours at 110° C. and calcined for 24 hours at 500° C. This borosilicate zeolite is composed of 94.2% by weight of $SiO_2$ and 2.32% by weight of $B_2O_3$.

Catalyst A (according to the invention)

50 g of this borosilicate zeolite are refluxed with 140 ml of 0.1 N HF for 1 hour, after which the product is filtered off, washed with water, dried at 110° C. for 16 hours, calcined at 500° C. for 5 hours and then converted to 3 mm tablets or to 2 mm extrudates.

Catalyst B (according to the invention)

50 g of the borosilicate zeolite, in the form of tablets or extrudates, are treated with 250 ml of 18% strength hydrochloric acid for 1 hour at 80° C., after which the product is filtered off, washed chloride-free with water, dried at 110° C. for 16 hours and calcined at 500° C. for 5 hours.

Catalyst C (according to the invention)

In the case of catalyst C, the measures described for catalysts A and B are combined, i.e. the borosilicate zeolite is treated with hydrofluoric acid and then with hydrochloric acid.

Crude methanol containing 20% by weight of water is converted quantitatively over these catalysts A, B and C under isothermal conditions, in a tube reactor, at 550° C. and a WHSV of $7.8h^{-1}$ (based on $CH_3OH$ employed). The yields, based on $CH_2$ employed, are shown in columns A, B and C of the Table.

To compare the yields, the catalysts below is employed; it is tested under the same reaction conditions as for catalysts A, B and C.

Catalyst D is obtained by extruding the borosilicate zeolite described above with boehmite in the ratio of 60:40. Drying is carried out at 110° C. for 16 hours and calcining at 500° C. for 16 hours.

| Catalyst | A | B | C | D |
|---|---|---|---|---|
| $C_2H_4$ | 12.1 | 6.7 | 11.9 | 12.0 |
| $C_3H_6$ | 40.8 | 42.9 | 43.4 | 32.9 |
| $C_4H_8$ | 21.1 | 20.9 | 22.8 | 16.1 |
| $CH_4$ | 1.4 | 1.2 | 1.5 | 7.9 |
| $C_2H_6$ | 0.3 | / | 0.3 | 0.6 |
| $C_3H_8$ | 1.6 | 0.6 | 1.4 | 2.1 |
| $C_4H_{10}$ | 1.0 | 1.0 | 0.9 | 1.2 |
| $C_5^+$-aliphatics | 10.7 | 20.3 | 12.3 | 9.4 |
| $C_6^+$-aromatics | 9.0 | 5.6 | 5.6 | 15.9 |
| Time-on-stream h | 14 | 12 | 90 | 7 |
| g of $CH_3OH$/g of catalyst | 109 | 94 | 702 | 55 |

We claim:

1. A process for the preparation of $C_2$-$C_4$-olefins by catalytic conversion of methanol and/or dimethyl ether in the presence of a zeolite catalyst at elevated temperatures, wherein the catalyst used is a pure borosilicate zeolite which has been tableted or extruded without a binder and treated with hydrofluoric acid and hydrochloric acid.

2. A process according to claim 1, wherein the catalyst is treated with 0.001–1N hydrofluoric acid.

3. A process as claimed in claim 1, wherein the catalyst is treated with 3–25% strength hydrochloric acid.

4. A process as claimed in claim 1, wherein the catalyst is treated with 0.001–1N hydrofluoric acid and then with 3–25% strength hydrochloric acid.

* * * * *